United States Patent [19]

Frangatos

[11] 4,331,546

[45] May 25, 1982

[54] LUBRICANT COMPOSITION CONTAINING PHOSPHITE-DIARYLAMINE-CARBONYL COMPOUND REACTION PRODUCT

[75] Inventor: Gerassimos Frangatos, Haddonfield, N.J.

[73] Assignee: Mobil Oil Corporation, New York, N.Y.

[21] Appl. No.: 212,295

[22] Filed: Dec. 3, 1980

Related U.S. Application Data

[63] Continuation-in-part of Ser. No. 7,872, Jan. 31, 1979, abandoned, and Ser. No. 115,961, Jan. 28, 1980, abandoned.

[51] Int. Cl.$^3$ .............................................. C10M 1/46
[52] U.S. Cl. .............................. 252/49.9; 252/400 A; 260/932; 260/970
[58] Field of Search ................ 252/49.9; 260/932, 970

[56] References Cited

U.S. PATENT DOCUMENTS

| | | | |
|---|---|---|---|
| 2,635,112 | 4/1953 | Fields | 252/49.9 X |
| 2,706,194 | 4/1955 | Morris et al. | 260/247 |
| 2,847,442 | 8/1958 | Sallman | 252/49.9 X |
| 2,870,190 | 1/1959 | Burgert et al. | 260/932 X |
| 3,257,479 | 6/1966 | Irani et al. | 260/932 X |
| 3,268,450 | 8/1966 | Sims et al. | 252/49.9 |
| 3,309,342 | 3/1967 | Friedman | 260/77.5 |
| 3,359,266 | 12/1967 | Maier | 260/246 |
| 3,549,728 | 12/1970 | Balde et al. | 252/49.9 X |
| 3,553,131 | 1/1971 | Hepplewhite et al. | 252/49.9 X |
| 3,553,265 | 1/1971 | Maier | 252/49.9 X |
| 4,060,571 | 11/1977 | Knapps et al. | 260/970 |
| 4,067,932 | 1/1978 | Muntz et al. | 260/927 |
| 4,112,014 | 9/1978 | Smith et al. | 260/945 |

FOREIGN PATENT DOCUMENTS 1168427  11/1961  Fed. Rep. of Germany ..... 252/49.9

OTHER PUBLICATIONS

Burger et al., Chem. Abs. 56, 1534f.
Hutton et al., Chem. Abs. 80, 30806v.

*Primary Examiner*—Andrew Metz
*Attorney, Agent, or Firm*—Charles A. Huggett; Michael G. Gilman; Claude E. Setliff

[57] ABSTRACT

The invention is directed to lubricants having therein an antioxidant quantity of a reaction product from phosphonates, amines and carbonyl-containing compounds.

8 Claims, No Drawings

LUBRICANT COMPOSITION CONTAINING PHOSPHITE-DIARYLAMINE-CARBONYL COMPOUND REACTION PRODUCT

BACKGROUND OF THE INVENTION

1. Cross-Reference to Related Applications:

This application is a continuation-in-part of U.S. application Ser. No. 7,872 filed Jan. 31, 1979 and U.S. application Ser. No. 115,961 filed Jan. 28, 1980 and both now abandoned.

2. Field of the Invention:

This invention relates to the inhibition of oxidation in lubricants. More particularly, the invention relates to lubricants to which has been added a phosphorus-containing antioxidant.

3. Discussion of the Prior Art:

Lubricants, such as lubricating oils and greases therefrom, are subject to oxidative deterioration at elevated temperatures or upon prolonged exposure to the elements. Such deterioration is evidenced, in many instances, by an increase in acidity and in viscosity. When the deterioration is especially severe, metal parts being lubricated will corrode. Additionally, severe oxidation often leads to a loss of lubrication properties of the lubricant, and, in especially severe cases, to complete break-down of the device being lubricated. In combatting oxidation, many additives have been used, but many of them are only marginally effective except at excessive concentrations, particularly when the lubricant is subjected to drastic oxidizing conditions.

No art is known that teaches or suggests the reaction product of the present compositions. It is well known that amines and other nitrogen-containing compounds have been used as antioxidants. For example, N-phenyl-alpha-naphthylamine has been used alone and in combination with other materials such as antioxidants. Phosphorus-containing compounds have also been used, generally not as antioxidants but as load carrying agents. For example, U.S. Pat. No. 3,986,967 discloses lubricants containing an organophosphorus-benzotriazole product as load carrying agent. U.S. Pat. No. 3,873,456 teaches a lubricant composition containing an extreme pressure amount of a complex phosphorus-containing compound.

SUMMARY OF THE INVENTION

In accordance with the invention, there is provided a lubricant composition comprising a major proportion of a lubricant and an antioxidant amount of a product made by reacting a dihydrocarbyl-phosphite with an amine and a carbonyl-containing compound. The invention also provides the product of such reaction.

DESCRIPTION OF SPECIFIC EMBODIMENTS

Because of the complex nature of the reaction that occurs when phosphites, amines and aldehydes are contacted, no precise structure can be assigned to the product. Thus, the final product will be referred to herein, both in the specification and the claims, as the product of the specified reaction.

However, it is believed that the reaction products will have at least some of the structures shown in the following, when using the illustrated reactants:

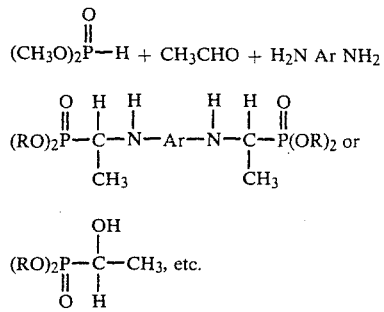

The dihydrocarbyl phosphites used herein have the formula:

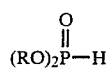

where R may be the same or different and is a hydrocarbyl group containing from 1 to 20 carbon atoms. The phosphites wherein R is lower alkyl, i.e., an alkyl having from 1 to 6 carbon atoms, are preferred. The useful reactants include those phosphites wherein R in the formula is methyl, ethyl, butyl or hexyl. Also included are those phosphites wherein R is an aryl group, such as phenyl or naphthyl, an alkaryl group such as a phenyl group or a naphthyl group having a $C_1-C_{10}$ alkyl group attached thereto, or an aralkyl group such as phenethyl group.

The amines can also be selected from secondary arylamines of the formula

wherein Ar is an aryl group having 6 to 14 carbon atoms and $R^1$ is an aryl group having 6 to 14 carbon atoms. The Ar and R groups may be further substituted with aryl or alkyl groups, where the aryl also has 6 to 14 carbon atoms and the alkyl group has 1 to 20 carbon atoms. "Aryl" may, for example, be phenyl, naphthyl or anthryl. This class includes such secondary arylamines as N-phenyl-alpha (or beta)-naphthylamine. Either or both aryl groups may be substituted with a methyl, ethyl, octyl, tetradecyl, octadecyl or an eicosyl group.

Another group of useful amines are the polyamines. These include the alkylene polyamines of the formula:

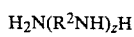

where $R^2$ is an alkylene group having 2 to 5 carbon atoms or an arylene group having 6 to 14 carbon atoms and z is 1 to 10. This includes phenylenediamine, for example. Further included are compounds of the structure

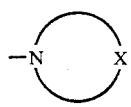

wherein the free valence may be taken up with hydrogen, a $C_1-C_5$ alkyl group or a $C_6-C_{14}$ aryl group, e.g., a methyl, ethyl, propyl, butyl, amyl, phenyl, naphthyl or anthryl group. The ring may be substituted with a $C_2-C_{20}$ alkyl group or a $C_6-C_{14}$ aryl group.

The alkylene polyamines include for example, ethylene diamine, diethylene triamine, triethylene tetramine, tetraethylene pentamine and the like, as well as those like dimethylene triamine.

The aldehyde useful in making the reaction product can be an aromatic aldehyde of the formula:

$R^3$—Ar—CHO wherein $R^3$ may be hydrogen, an alkyl group containing 1 to 24 carbon atoms, —OH —$NO_2$, Cl, Br, —SH, —CN and Ar is an aryl group containing 6 to 14 carbon atoms. Preferably Ar is phenyl. This group is exemplified by substituted benzaldehyde with aforementioned substituents. Preferred is o-hydroxybenzaldehyde (salicylaldehyde). The aldehyde can also be one having the formula:

$R^4$CHO wherein $R^4$ is an alkyl having from 1 to 24 carbon atoms. Within this group are acetaldehyde (ethanal), propionaldehyde (propanal), butyraldehyde (butanal) heptaldehyde (heptanal), and so forth. Preferred is haptanal.

It is contemplated that, in addition to aldehydes, ketones can be used as a source of carbonyl groups. They may have the formula $R^5COR^6$ wherein $R^5$ and $R^6$ may be the same or different and may be an alkyl or haloalkyl containing from 1 to 20 carbon atoms or an aryl having 6 to 14 carbon atoms. As members of his groups, there may be named acetone, methyl ethyl ketone, methyl-n-propyl ketone, diethyl ketone, hexanone-2, hexanone-3, methylt-butyl ketone, di-n-propyl ketone, diisopropyl ketone, diisobutyl ketone, di-n-amyl ketone, stearone, chloracetone, dichloroacetone, cyclohexanone, benzophenone and the like.

The reactants are preferably used in equimolar quantities. That is, the reaction mixture should contain at least one mole each of phosphite, amine and carbonyl-containing compound. The invention, however, contemplates products made by using ratios of respective reactants, i.e. phosphite, aldehyde and nitrogen compounds, within the ratios of 1:1:1 to 1:5:25.

The method of mixing the reactants for carrying out the reaction is not critical. They may be mixed together all at once before heating to begin the reaction. Further, two of the reactants may be mixed with solvents and heated, with addition of the third reactant while heating. This will become clear from the examples below.

The temperature of reaction will depend upon the solvent used, since the reaction will generally be run at the temperature of reflux. The temperature is not believed to be critical and the reaction can be run over a wide range of from about 80° C. to about 225° C., preferably from about 80° C. to about 150° C. Examples of useful solvents are toluene, benzene, xylene, cyclohexane, ethanol and the like.

Times of reaction are not critical, but they will vary depending upon the size and complexity of the reactants. Under normal conditions, the reaction with the contemplated reactants can be completed in from about 1 hour to about 10 hours, preferably from about 1 hour to about 3 hours. A solvent is desirable in some cases where strongly exothermic reaction occurs and generally useful for the azeotropic removal of the water formed during the condensation reaction. Where a solvent is used, it should be one in which the products are soluble and which can be relatively easily removed.

Having described the invention in general aspects, the following examples are offered as specific illustrations.

EXAMPLE 1

Into a reactor were placed about 50 parts of dimethylsulfoxide, 22 parts of toluene, 38.8 parts of dibutyl phosphonate [$(C_4H_9O)_2POH$], 22.8 parts of heptanal and 10.8 parts of p-phenylenediamine (molar ratio of 2:2:1, respectively). The mixture was heated at 140°–145° C. for 2 hours. About 3.6 parts of water were collected in the water trap. The reaction mixture was left under nitrogen at room temperature overnight.

EXAMPLE 2

A mixture of 0.2 mole of dibutyl phosphite, 0.2 mole of morpholine

0.2 mole of paraformaldehyde, 2 g. of glacial acetic acid and 150 ml. of ethanol was placed in a reactor, was stirred and refluxed under nitrogen for 4 hours. A homogeneous solution was obtained, from which the solvent and other volatiles were removed under reduced pressure at a pot temperature of up to 130° C. The residue was treated with charcoal and filtered. The IR Spectrum of the product showed neither P—H nor CO present in the product.

EXAMPLE 3

A mixture of 19.4 g. (0.1 mole) of dibutyl phosphite, 11.4 g. (0.1 mole) of heptanal, 21.9 g. (0.1 mole) of N-phenyl-alpha-naphthylamine and 120 ml. of toluene was heated to reflux and refluxed for 3 hours, during which time 1.6 ml. of water (theoretical) was recovered. The solvent was stripped off under reduced pressure to a pot temperature of 130° C., yielding 51.0 g. of product. The IR Spectrum showed a small amount of residual P—H and N—H adsorption.

EXAMPLE 4

Into a reactor were placed 38.8 parts of dibutyl phosphonate, 17.4 parts of morpholine and 78 parts of cyclohexane and the contents were heated to 65° C. 21.2 parts of benzaldehyde (1:1:1 molar ratio) were added, producing an exothermic reaction. The reaction mixture was heated to reflux temperature, and refluxing under nitrogen, with stirring, was continued for 2 hours. About 3.6 parts of water was collected in the water trap. The solvent was stripped off under reduced pressure to give 72 parts of reaction product.

EXAMPLE 5

A mixture of 0.2 mole of dibutyl phosphite, 0.2 mole of heptanal and 150 ml. of toluene was heated to 80° C. with stirring, and 0.2 mole of N-methylaniline was added thereto over a period of 20 minutes. This was brought to reflux temperature and 3.6 ml. of water was collected during the reaction over a 2-hour period. The solvent was stripped off under reduced pressure to a final pot temperature of 140° C., leaving a clear viscous liquid weighing 78.0 g.

EXAMPLE 6

A mixture of tetraethylenepentamine (18.9 parts), dibutyl phosphonate (97.0 parts) benzaldehyde (53.0 parts) and 130 parts of toluene were placed into a reactor equipped with a stirrer, reflux condenser, nitrogen inlet tube and water trap. The reaction mixture was stirred and refluxed, under nitrogen, for 3 hours. 9 parts of water were collected. The solvent and other volatiles were distilled off under reduced pressure to a final pot temperature of 135° C., yielding 160 parts of reaction product.

EVALUATION OF PRODUCTS

The utility of the products as antioxidants is demonstrated by comparative tests made on a lubricating oil containing one of the additives and the same oil without any additive.

Antioxidant Test

In this test, the product is added to a solvent refined 130″ mineral lubricating oil. The oil is then heated to 425° F. and dry air at a rate of 10 pounds per hour is passed through it in the presence of iron, copper, aluminum and lead. After 40 hours, the neutralization number (NN) for each oil composition is obtained according to ASTM Method D741-1. The effectiveness of the additives is revealed by comparison of the control of viscosity increase (kinematic viscosity, KV), and control of acids (change in neutralization number), with the additive-free oil. Results of a series of tests are shown in Table I, following:

TABLE I

| Additive | Conc. Wt. Percent | ΔKV, % @210° F. | ΔNN |
|---|---|---|---|
| None | — | 2.468 | 6.85 |
| PAN | 0.5 | 2.203 | 6.81 |
|  | 1.0 | 1.716 | 4.30 |
| Example 3 | 1.0 | 0.333 | 0.06 |
|  | 2.0 | 0.437 | 0.47 |
| Example 5 | 1.0 | 4.386 | 11.99 |
|  | 2.0 | 2.162 | 6.19 |
|  | 3.0 | 1.149 | — |

Rust Test

The test used was the one described in detail in ASTM D1743, except that 5% synthetic sea water was employed instead of the distilled water called for and the duration of the test was 24 hours rather than 48 hours. The grease was a lithium soap grease having a base oil with a viscosity at 400° C. of 150 Cs.

Table II below summarizes the results.

TABLE II

| Product | % Wt. of Product | Synthetic Sea Water %, Conc. | Test Time, Hrs. | Estimated % of Surface Rusted | |
|---|---|---|---|---|---|
| | | | | Test #1 | Test #2 |
| Example 1 | 5 | 100 | 48 | 5 | 10 |
|  | 5 | 5 | 24 | 5 | 5 |
| Example 4 | 5 | 100 | 48 | 15 | 20 |
|  | 5 | 5 | 24 | 1 | 1 |
| Example 6 | 5 | 100 | 48 | 20 | 20 |
|  | 5 | 5 | 24 | 10 | 10 |
| None | — | 100 | 48 | 80 | 90 |
| None | — | 5 | 24 | 10 | 15 |

The lubricants for which the compounds of this invention find utility include petroleum products and synthetic fluids of lubricating viscosity and greases therefrom. In the latter class may be included synthetic ester lubricants, such as those formed from monohydric alcohols and dicarboxylic acids, glycols or glycerols with monocarboxylic acids, and pentaerythritols with carboxylic acids, including alcohols having from about 4 to about 20 carbon atoms, and carboxylic acids having from 2 to about 18 carbon atoms. Many synthetic esters may have mixed alcohols or carboxylic acids. Commonly may be included 2-ethylhexyl sebacate, trimethylolpropane trioctanoate, and especially pentaerythritol esters of valeric acids, isovaleric acid, caproic acid, carprylic acids, penargonic acid, capric acid, and the like. Of special interest is a mixed pentaerythritol ester of an equimolar proportion of commercial valeric acid (containing isovaleric acid) and penargonic acid. Other synthetic fluids include liquid polyolefins, alkylene oxide fluids, silicone fluids, polyacetals, and simple and complex hydrocarbons of stable fluid viscosities.

I claim:

1. A product of reaction formed by reacting at least equimolar quantities of (1) a dialkyl phosphite of the formula:

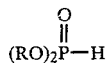

wherein R is a $C_1-C_6$ alkyl group, a phenyl or naphthyl group, a phenyl or naphthyl group having a $C_1-C_{10}$ alkyl group attached thereto or a phenethyl group, (2) an amine of the formula:

wherein Ar and $R^1$ are aryl groups containing 6 to 14 carbon atoms and (3) a carbonyl-containing compound selected from the group consisting of the formula:

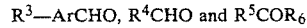

wherein $R^3$ is hydrogen, a $C_1-C_{24}$ alkyl group, —OH, —$NO_2$, —Cl, —Br, —SH or —CN, Ar is an aryl group containing 6 to 14 carbon atoms, $R^4$ is a $C_1-C_{24}$ alkyl group and $R^5$ and $R^6$ are the same or different $C_1-C_{20}$ alkyl groups, $C_1-C_{20}$ haloalkyl groups or $C_6-C_{14}$ aryl groups, wherein said aryl is phenyl, naphthyl or anthryl.

2. The product of claim 1 wherein R is an alkyl having 1 to 6 carbon atoms.

3. The product of claim 1 wherein R is an aryl group.

4. The product of claim 1 wherein the reactants are dibutyl phosphite, heptanal and N-phenyl-, alpha-naphthylamine.

5. A lubricant composition comprising a major proportion of a lubricant and an antioxidant amount of a product of reaction formed by reacting at least equimolar quantities of (1) a dialkyl phosphite of the formula:

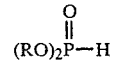

wherein R is a $C_1-C_6$ alkyl group, a phenyl or naphthyl group, a phenyl or naphthyl group having a $C_1-C_{10}$ alkyl group attached thereto or a phenethyl group, (2) an amine of the formula:

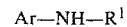

wherein Ar and $R^1$ are aryl groups containing 6 to 14 carbon atoms and (3) a carbonyl-containing compound selected from the group consisting of the formula:

$R^3$—ArCHO, $R^4$CHO and $R^5$COR$^6$ wherein $R^3$ is hydrogen, a $C_1$-$C_{24}$ alkyl group, —OH, —NO$_2$, —Cl, —Br, —SH or —CN, Ar is an aryl group containing 6 to 24 carbon atoms, $R^4$ is a $C_1$-$C_{24}$ alkyl group and $R^5$ and $R^6$ are the same or different $C_1$-$C_{14}$ aryl groups, wherein said aryl is phenyl, naphthyl or anthryl.

6. The composition of claim 5 wherein R is an alkyl having 1 to 6 carbon atoms.

7. The composition of claim 5 wherein the R group is an aryl group.

8. The composition of claim 5 wherein the product of reaction is made by reacting dibutyl phosphonate, heptanal and N-phenyl-alpha-naphthylamine.

* * * * *

UNITED STATES PATENT AND TRADEMARK OFFICE
CERTIFICATE OF CORRECTION

PATENT NO. : 4,331,546
DATED : May 25, 1982
INVENTOR(S) : GERASSIMOS FRANGATOS

It is certified that error appears in the above-identified patent and that said Letters Patent are hereby corrected as shown below:

Column 3, line 15, "o-hydroxybenzaldehyde" should be

--o-hydroxybenzaldehyde--.

Column 3, lines 23, 24, "haptanal" should be --heptanal--.

Signed and Sealed this

Fourteenth Day of September 1982

[SEAL]

Attest:

Attesting Officer

GERALD J. MOSSINGHOFF

Commissioner of Patents and Trademarks